(12) United States Patent
Venkatesh et al.

(10) Patent No.: US 11,944,442 B2
(45) Date of Patent: Apr. 2, 2024

(54) READING EEPROM DATA FROM AN EEPROM LEADSET

(71) Applicant: Drägerwerk AG & Co. KGaA, Lübeck (DE)

(72) Inventors: Arvind K. Venkatesh, Lexington, MA (US); Georgios Kokovidis, Waltham, MA (US)

(73) Assignee: Drägerwerk AG & Co. KGaA (DE)

( * ) Notice: Subject to any disclaimer, the term of this patent is extended or adjusted under 35 U.S.C. 154(b) by 305 days.

(21) Appl. No.: 17/459,233

(22) Filed: Aug. 27, 2021

(65) Prior Publication Data

US 2022/0133204 A1     May 5, 2022

Related U.S. Application Data

(60) Provisional application No. 63/106,933, filed on Oct. 29, 2020.

(51) Int. Cl.

| | |
|---|---|
| A61B 5/30 | (2021.01) |
| A61B 5/301 | (2021.01) |
| A61B 5/304 | (2021.01) |
| A61B 5/308 | (2021.01) |
| A61B 5/333 | (2021.01) |
| G11C 16/04 | (2006.01) |
| G11C 16/26 | (2006.01) |

(52) U.S. Cl.
CPC .............. *A61B 5/303* (2021.01); *A61B 5/301* (2021.01); *A61B 5/304* (2021.01); *A61B 5/308* (2021.01); *A61B 5/333* (2021.01); *G11C 16/26* (2013.01); *G11C 16/0433* (2013.01)

(58) Field of Classification Search
None
See application file for complete search history.

(56) References Cited

U.S. PATENT DOCUMENTS

| | | | | |
|---|---|---|---|---|
| 5,617,868 | A * | 4/1997 | Harada | A61B 5/02241 |
| | | | | 600/490 |
| 5,995,855 | A * | 11/1999 | Kiani | A61B 5/14552 |
| | | | | 600/323 |
| 6,038,477 | A * | 3/2000 | Kayyali | A61N 1/32 |
| | | | | 607/2 |
| 6,246,902 | B1 * | 6/2001 | Naylor | A61B 5/30 |
| | | | | 600/509 |
| 7,675,190 | B1 * | 3/2010 | Muller | H04B 3/56 |
| | | | | 307/3 |

(Continued)

*Primary Examiner* — Carl H Layno
*Assistant Examiner* — Manolis Pahakis
(74) *Attorney, Agent, or Firm* — Design IP

(57) ABSTRACT

An electrocardiogram (ECG) extension cable includes a first connector configured to be electrically coupled to a physiological monitoring device, a second connector configured to be electrically coupled to an ECG lead set including a processor, an input/output (I/O) wire configured to transmit data between the physiological monitoring device and the processor, a ground wire that establishes a ground path between the first connector and the second connector, a series protection element coupled in series along the ground wire, a bypass path coupled to the ground wire in parallel to the series protection element, and a switching element arranged along the bypass path and configured to redirect the ground path along the bypass path, thereby bypassing the series protection element.

25 Claims, 3 Drawing Sheets

(56) References Cited

U.S. PATENT DOCUMENTS

| | | | | |
|---|---|---|---|---|
| 8,634,901 | B2* | 1/2014 | Callahan | A61B 5/318 607/9 |
| 11,331,508 | B1* | 5/2022 | Cowan | A61N 1/3968 |
| 2009/0093687 | A1* | 4/2009 | Telfort | A61B 5/0215 600/300 |
| 2010/0069108 | A1* | 3/2010 | Kannar | H04W 36/30 455/513 |
| 2010/0241206 | A1* | 9/2010 | Truex | A61B 5/7203 607/116 |
| 2012/0130229 | A1* | 5/2012 | Zellers | A61B 5/062 600/424 |
| 2014/0088394 | A1* | 3/2014 | Sunderland | A61B 5/6843 600/373 |
| 2014/0266775 | A1* | 9/2014 | Moon | A61B 5/4343 340/870.01 |
| 2014/0343625 | A1* | 11/2014 | O Laighin | A61N 1/36034 607/48 |
| 2015/0134031 | A1* | 5/2015 | Moffitt | A61N 1/37264 607/62 |
| 2016/0245670 | A1* | 8/2016 | Nelson | A61B 5/283 |
| 2017/0125892 | A1* | 5/2017 | Arbabian | A61B 5/0028 |
| 2018/0338696 | A1* | 11/2018 | Deliwala | A61B 5/6801 |
| 2020/0000355 | A1* | 1/2020 | Khair | A61B 5/296 |
| 2020/0069953 | A1* | 3/2020 | Finch | A61N 1/0484 |
| 2022/0287644 | A1* | 9/2022 | Batzer | A61B 5/28 |

\* cited by examiner

READING EEPROM DATA FROM AN EEPROM LEADSET

BACKGROUND

Patient monitors are devices that are configured to receive physiological data from another device and either display a patient's physiological data, monitor a patient's physiological data, or both. A patient monitor may be configured to be worn by a patient, may be a hand-held device, may be docked to or undocked from a larger unit such as a monitor mount, and, thus, may be transportable. For example, a monitor mount may be a larger patient monitor or a console that has a docking interface or docking receptacle to which the patient monitor can be removably docked.

A patient monitor may be implemented to monitor cardiac signals from a patient via electrocardiogram (ECG) sensors connected to an ECG lead set. Commonly used ECG lead set configurations include 3-lead, 5-lead, 6-lead and 12-lead configurations. In a 12-lead ECG configuration, for example, ten electrodes (i.e., sensors) are placed on predetermined locations of the skin of the patient body. The overall magnitude of the heart's electrical potential is then measured from twelve different angles ("leads") and is recorded over a period of time (e.g., 10 seconds). In this way, the overall magnitude and direction of the heart's electrical activity is captured throughout the heartbeat.

Depending on the patient's medical conditions and/or clinical needs, the patient who is under the monitoring can also be in different medical environments or under medical procedures, for example, an operation. Electrosurgical units (ESU) are routinely used in operating rooms and are known to interfere with the monitoring of patients' bio-potential signals (e.g. ECG signals). An ESU applies large amplitude and high frequency signals to the patient's body for operations, where these signals interfere with the bio-potential signals of the patient. Additionally, in an operating room environment, with an ESU being used to perform electrosurgery, significant current could flow through the patient causing patient burns (i.e., ESU burns) and other safety problems.

SUMMARY

One or more embodiments provide an electrocardiogram (ECG) extension cable that includes a first connector configured to be electrically coupled to a physiological monitoring device; a second connector configured to be electrically coupled to an ECG lead set including a processor; an input/output (I/O) wire configured to transmit data between the physiological monitoring device and the processor; a ground wire that establishes a ground path between the first connector and the second connector; a series protection element coupled in series along the ground wire; a bypass path coupled to the ground wire in parallel to the series protection element; and a switching element arranged along the bypass path and configured to redirect the ground path along the bypass path, thereby bypassing the series protection element.

One or more embodiments provide an ECG system, including: an ECG lead set including a plurality of leads configured to measure ECG electrical signals and a processor configured to store data; a physiological monitoring device configured to receive and monitor the ECG electrical signals; and an ECG extension cable coupled to and between the ECG lead set and the physiological monitoring device. The ECG extension cable includes: a first connector configured to be electrically coupled to the physiological monitoring device; a second connector configured to be electrically coupled to the ECG lead set; an input/output (I/O) wire configured to transmit the data between the physiological monitoring device and the processor; a ground wire that establishes a ground path between the first connector and the second connector; a series protection element coupled in series along the ground wire; a bypass path coupled to the ground wire in parallel to the series protection element; and a switching element arranged along the bypass path and configured to redirect the ground path along the bypass path, thereby bypassing the series protection element.

One or more embodiments provide a method for transmitting data in an ECG system, the method including: connecting an ECG lead set to a physiological monitoring device via an ECG extension cable, wherein the ECG lead set includes a plurality of leads configured to measure ECG electrical signals and a processor configured to store data; detecting an initial connection being made between the ECG lead set to the physiological monitoring device; and in response to detecting the initial connection, bypassing a series protection element coupled in series along a ground wire of the ECG extension cable such that a ground path is redirected through a switching element of the ECG extension cable, thereby bypassing the series protection element.

BRIEF DESCRIPTION OF THE DRAWINGS

In the drawings, like reference numbers generally indicate identical, functionally similar, and/or structurally similar elements.

DETAILED DESCRIPTION

Figure 1:
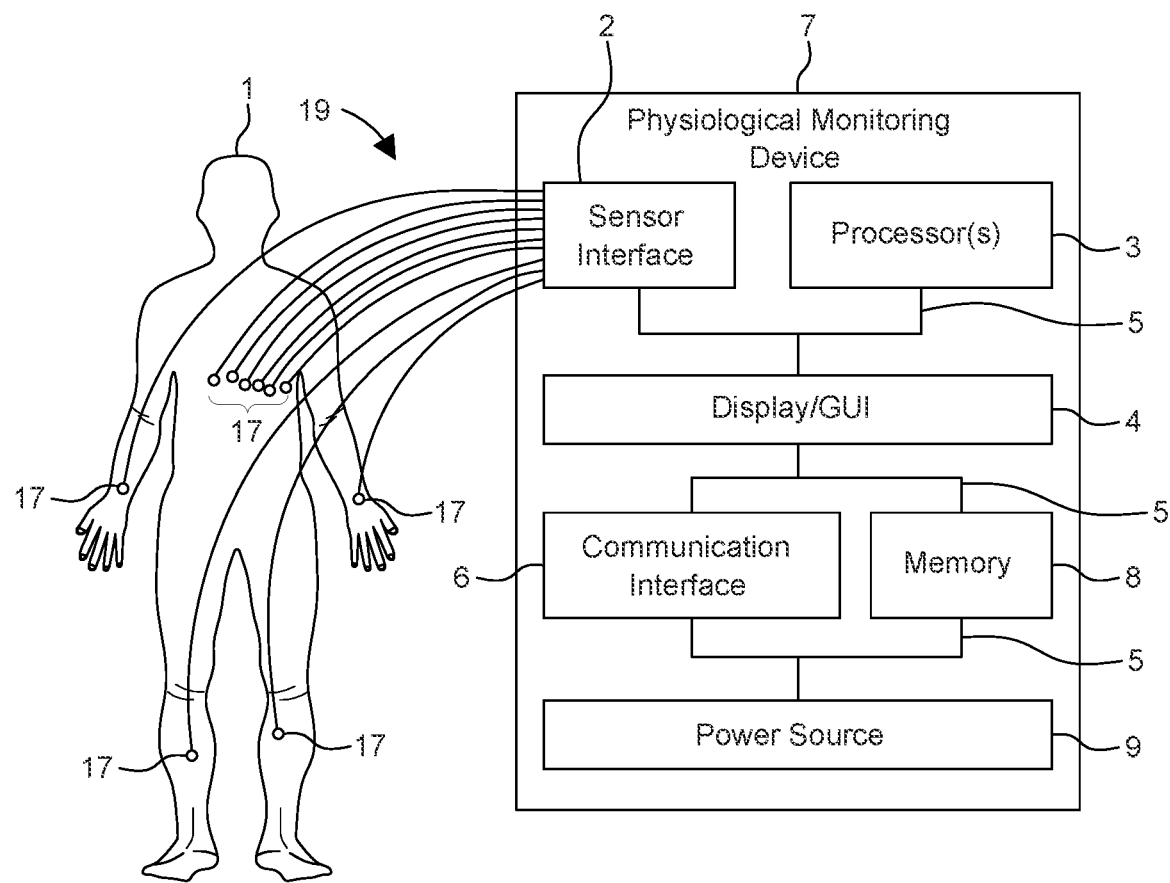
FIG. 1 shows a physiological monitoring system according to one or more embodiments.

In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

Instructions may be executed by one or more processors, such as one or more central processing units (CPU), digital signal processors (DSPs), general purpose microprocessors, application specific integrated circuits (ASICs), field programmable logic arrays (FPGAs), or other equivalent integrated or discrete logic circuitry. Accordingly, the term "processor," as used herein refers to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. A "controller," including one or more processors, may use electrical signals and digital algorithms to perform its receptive, analytic, and control functions, which may further include corrective functions. Thus, a controller is a specific type of processing circuitry, comprising one or more processors and memory, that implements control functions by way of generating control signals.

Signal conditioning, as used herein, refers to manipulating an analog signal in such a way that the signal meets the requirements of a next stage for further processing. Signal conditioning may include converting from analog to digital (e.g., via an analog-to-digital converter), amplification, filtering, converting, biasing, range matching, isolation and any other processes required to make a sensor output suitable for processing after conditioning.

FIG. 1 shows a physiological monitoring system according to one or more embodiments. As shown in FIG. 1, the system includes a patient monitor 7 (i.e., a physiological monitoring device) capable of receiving physiological data from various sensors 17 connected to a patient 1.

In general, it is contemplated by the present disclosure that the patient monitor 7 includes electronic components and/or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the patient monitor 7 may be adapted to execute any operating system, including Linux, UNIX, Windows Server, etc., as well as virtual machines adapted to virtualize execution of a particular operating system, including customized and proprietary operating systems. The patient monitor 7 may be further equipped with components to facilitate communication with other computing devices over one or more network connections, which may include connections to local and wide area networks, wireless and wired networks, public and private networks, and any other communication network enabling communication in the system.

As shown in FIG. 1, the patient monitor 7 is, for example, a patient monitor implemented to monitor various physiological parameters of the patient 1 via the sensors 17. The patient monitor 7 includes a sensor interface 2, one or more processors 3, a display/graphical user interface (GUI) 4, a communication interface 6, a memory 8, and a power source 9. The sensor interface 2 can be implemented in hardware or combination of hardware and software and is used to connect via wired and/or wireless connections 19 to one or more sensors 17 for gathering physiological data from the patient 1. The sensors 17 may be physiological sensors and/or medical devices configured to measure one or more of the physiological parameters and output the measurements via a corresponding one or more connections 19 to the sensor interface 2. Thus, the connections 19 represent one or more wired or wireless communication channels configured to at least transmit sensor data from a corresponding sensor 17 to the sensor interface 2.

By way of example, sensors 17 may include electrodes that are attached to the patient 1 for reading electrical signals generated by or passed through the patient 1. Sensors 17 may be configured to measure vital signs, measure electrical stimulation, measure brain electrical activity such as in the case of an electroencephalogram (EEG), measure blood characteristics using absorption of light, for example, blood oxygen saturation fraction from absorption of light at different wavelengths as it passes through a finger, measure a carbon dioxide ($CO_2$) level and/or other gas levels in an exhalation stream using infrared spectroscopy, measure oxygen saturation on the surface of the brain or other regions, measure cardiac output from invasive and noninvasive blood pressure, measure temperature, measure induced electrical potentials over the cortex of the brain, measure blood oxygen saturation from an optical sensor coupled by fiber to the tip of a catheter.

The data signals from the sensors 17 include, for example, sensor data related to an electrocardiogram (ECG), non-invasive peripheral oxygen saturation (SpO2), non-invasive blood pressure (NIBP), body temperature, end tidal carbon dioxide (etCO2), apnea detection, and/or other physiological data, including those described herein. The one or more processors 3 are used for controlling the general operations of the patient monitor 7, as well as processing sensor data received by the sensor interface 2. Each one of the one or more processors 3 can be, but are not limited to, a central processing unit (CPU), a hardware microprocessor, a multicore processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the patient monitor 7.

The display/GUI 4 is configured to display various patient data, sensor data, and hospital or patient care information, and includes a user interface implemented for allowing interaction and communication between a user and the patient monitor 7. The display/GUI 4 includes, but is not limited to, a keyboard, a liquid crystal display (LCD), cathode ray tube (CRT) display, thin film transistor (TFT) display, light-emitting diode (LED) display, high definition (HD) display, or other similar display device that may include touch screen capabilities. The display/GUI 4 also provides a means for inputting instructions or information directly to the patient monitor 7. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators).

The communication interface 6 enables the patient monitor 7 to directly or indirectly communicate with one or more computing networks and devices, including one or more sensors 17, workstations, consoles, computers, monitoring equipment, alert systems, and/or mobile devices (e.g., a mobile phone, tablet, or other hand-held display device). The communication interface 6 can include various network cards, interfaces, communication channels, cloud, antennas, and/or circuitry to enable wired and wireless communications with such computing networks and devices. The communication interface 6 can be used to implement, for example, a Bluetooth connection, a cellular network connection, and/or a Wi-Fi connection with such computing networks and devices. Example wireless communication connections implemented using the communication interface 6 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol).

Additionally, the communication interface 6 can enable direct (e.g., device-to-device) communications (e.g., messaging, signal exchange, etc.) to the patient monitor 7 using, for example, a universal serial bus (USB) connection or other communication protocol interface. The communication interface 6 can also enable direct device-to-device connection to other device such as to a tablet, computer, or similar electronic device; or to an external storage device or memory.

The memory 8 can be a single memory device or one or more memory devices at one or more memory locations that include, but is not limited to, a random access memory (RAM), a memory buffer, a hard drive, a database, an erasable programmable read only memory (EPROM), an electrically erasable programmable read only memory (EEPROM), a read only memory (ROM), a flash memory, hard disk, various layers of memory hierarchy, or any other non-transitory computer readable medium. The memory 8 can be used to store any type of instructions and patient data associated with algorithms, processes, or operations for controlling the general functions and operations of the patient monitor 7.

The power source 9 can include a self-contained power source such as a battery pack and/or include an interface to be powered either directly or indirectly through an electrical outlet. The power source 9 can also be a rechargeable battery that can be detached allowing for replacement. In the case of a rechargeable battery, a small built-in back-up battery (or super capacitor) can be provided for continuous power to be provided to the patient monitor 7 during battery replacement. Communication between the components of the patient monitor 7 (e.g., components 2, 3, 4, 6, 8, and 9) are established using an internal bus 5.

Accordingly, the patient monitor 7 is attached to one or more of several different types of sensors 17 configured to measure and readout physiological data related to the patient 1 (e.g., as shown on the left side of FIG. 1). One or more sensors 17 may be attached to patient monitor 7 by, for example, a wired connection coupled to the sensor interface 2. Additionally, or alternatively, one or more sensors 17 may be a wireless sensor that is communicatively coupled to the patient monitor 7 via the communication interface 6, which includes circuitry for receiving data from and sending data to one or more devices using, for example, a Wi-Fi connection, a cellular network connection, and/or a Bluetooth connection.

The data signals from the sensors 17 received by the patient monitor 7 may include sensor data related to, an ECG.

The data signals received from an ECG sensor can be analog signals. For example, the data signals for the ECG are input to the sensor interface 2, which can include an ECG data acquisition circuit. Both the ECG data acquisition circuit may include amplifying and filtering circuitry as well as analog-to-digital (A/D) circuitry that converts the analog signal to a digital signal using amplification, filtering, and A/D conversion methods. In the event that an ECG sensor is a wireless sensor, the sensor interface 2 may receive the data signals from a wireless communication module. Thus, a sensor interface is a component configured to interface with one or more sensors 17 and receive sensor data therefrom.

The processing performed by the ECG data acquisition circuit may generate analog data waveforms or digital data waveforms that are analyzed by a microcontroller. The microcontroller may be one of the processors 3. The microcontroller, for example, analyzes the digital waveforms to identify certain digital waveform characteristics and threshold levels indicative of conditions (abnormal and normal) of the patient 1 using one or more monitoring methods. A monitoring method may include comparing an analog or a digital waveform characteristic or an analog or digital value to one or more threshold values and generating a comparison result based thereon. The microcontroller is, for example, a processor, an FPGA, an ASIC, a DSP, a microcontroller, or similar processing device. The microcontroller includes a memory or uses a separate memory 8. The memory is, for example, a RAM, a memory buffer, a hard drive, a database, an EPROM, an EEPROM, a ROM, a flash memory, a hard disk, or any other non-transitory computer readable medium.

The memory stores software or algorithms with executable instructions and the microcontroller can execute a set of instructions of the software or algorithms in association with executing different operations and functions of the patient monitor 7 such as analyzing the digital data waveforms related to the data signals from the sensors 17.

Figure 2:
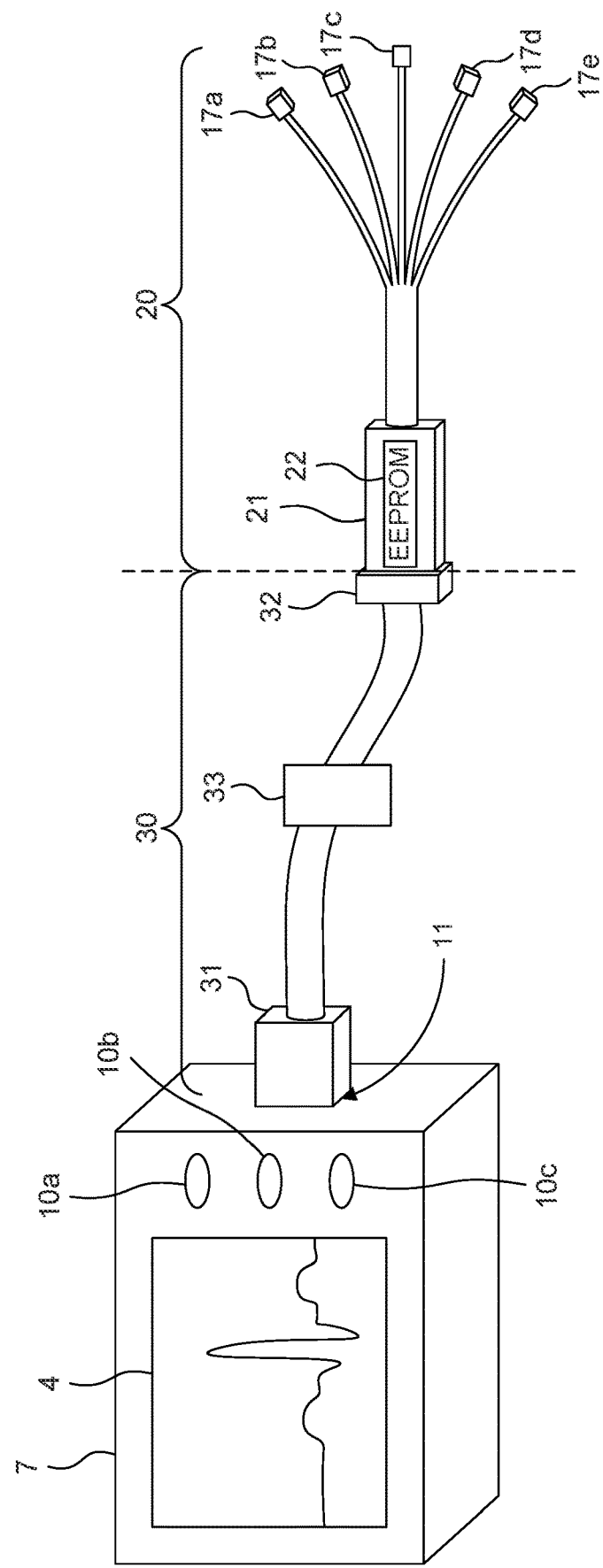
FIG. 2 shows an electrocardiogram (ECG) cable system and ECG monitoring device according to one or more embodiments.

FIG. 2 shows an ECG cable system and ECG monitoring device according to one or more embodiments. In particular, the ECG monitor device is the patient monitor 7 that has ECG monitoring functionalities. The patient monitor 7 is configured to monitor cardiac signals from a patient via ECG sensors connected to an ECG lead set. Commonly used ECG lead set configurations include 3-lead, 5-lead, 6-lead and 12-lead configurations. In a 12-lead ECG configuration, for example, ten electrodes (i.e., sensors) are placed on predetermined locations of the skin of the patient body. The overall magnitude of the heart's electrical potential is then measured from twelve different angles ("leads") and is recorded over a period of time (e.g., 10 seconds). In this way, the overall magnitude and direction of the heart's electrical activity is captured throughout the heartbeat.

According to one or more embodiments, an ECG application may use an ECG lead set that has multiple electrodes at one end and uses an ECG extension cable that connects the other end of the ECG lead set to the patient monitor, thereby allowing the distance between patient and the patient monitor to be increased while the lead set is in use.

As defined herein, the ECG lead set 20 may be a "smart" cable in that it comprises a processor (e.g., an EEPROM 22) that is embedded therein and can operate to some extent interactively and autonomously with another device. The processor may be an EEPROM, a central processing units (CPU), a digital signal processor (DSPs), a general purpose microprocessor, an application specific integrated circuit (ASIC), a field programmable logic array (FPGA), or other equivalent integrated or discrete logic circuitry. For example, the processor may be embedded in a connector of the ECG lead set. The processor is configured to store data relevant to the ECG lead set and the patient monitor is capable of carrying out both read and write operations with respect to the stored data (e.g., EEPROM data).

An electrosurgical unit (ESU) is a medical device designed to make precise surgical incisions using an active-electrode pencil, which is heated via electric current in order to cauterize tissue and stimulate coagulation of bodily fluids. In an operating room environment, with an ESU being used to perform electrosurgery, significant current could flow through the patient causing patient burns (i.e., ESU burns) and other safety problems. According to one or more embodiments, a series protection element such as a resistor or an inductor is added to the conductors that are in close proximity with the patient in order to protect the patient during a procedure in which an ESU is used. In the case that an ECG extension cable is used, the series protection element is added to the ECG ground line of the ECG extension cable. However, this series protection element interferes with data being read from the processor by, for example, attenuating the data signal, and prevents the data from being transmitted properly between the processor of the ECG lead set 20 and the patient monitor 7, including both read and write operations.

Thus, an ECG extension cable that provides ESU protection via an ESU safety element (i.e., series protection element) in its ground path and that also enables EEPROM data to be successfully read from and written to the EEPROM of the ECG lead set may be desirable.

The patient monitor 7 includes the display 4 and optionally, user input buttons 10a, 10b, and 10c for receiving user input. The patient monitor 7 further includes a cable interface 11, such as a cable port, that is configured to receive a cable and electrically connect a cable to the patient monitor 7. Thus, the cable interface 11 may further include a number or pins for engaging with pin holes of the cable or a number of pin holes for engaging with pins of the cable, depending on the configuration. Any cable interface may be used, including any male-to-female connector interface or female-to-male connector interface.

The patient monitor 7 is configured to receive physiological data, in this case ECG data, from the connected cable, process the physiological data, and display processed physiological data onto the display 4.

The cable system includes an ECG lead set 20 and an ECG extension cable 30. The cable system represents the one or more of the connections 19 shown in FIG. 1. In this case, the ECG lead set 20 includes five leads with each lead terminating at a sensor (e.g., an electrode) 17a-17e that is attached to the patient for measuring ECG data. It is noted that in practice, the ECG lead set 20 can include any number of leads. The ECG lead set 20 has a connector 21. The connector 21 is configured to be connected directly to the patient monitor 7. The connector 21 is also configured to be connected the ECG extension cable 30. The ECG extension cable 30 is used, for example, when the ECG lead set 20 is not long enough to fully extend from the patient to the patient monitor 7. Thus, the connector 21 is an interface that is configured to be electrically coupled to the patient monitor 7 and to the ECG extension cable 30. Any connector interface may be used for the connector 21, including any male-to-female connector interface or female-to-male connector interface.

In the present example, the ECG lead set 20 is a smart cable that comprises an EEPROM 22 that is embedded therein and can operate to some extent interactively and autonomously with another device. The EEPROM 22 may be, for example, integrated inside the connector housing of the connector 21. The EEPROM 22 is configured to store data relevant to the ECG lead set 20, including information such as a number of leads, authentication information, number of use information, and so forth.

The number of leads of various types of ECG lead sets can vary. For example, existing ECG lead sets have anywhere between 3-wires to 10-wires. However, any number of leads is possible. The patient monitor 7 requires information regarding how many leads are present in the ECG lead set to allow for proper processing and display of ECG data. The EEPROM 22 may be configured to send this information autonomously after it autonomously detects a connection made to the patient monitor 7 and after a series protection element 34 is bypassed, as described below.

Reading the EEPROM 22 is also critical for detecting whether an ECG lead set is correctly plugged into the patient monitor 7. The EEPROM 22 may store authentication information that allows the patient monitor 7 to verify that the ECG lead set is authentic and not a counterfeit. Furthermore, the EEPROM 22 may store usage information indicating its number of uses and provide the number of uses to the patient monitor 7 so that the patient monitor 7 can check whether the ECG lead set has exceeded its lifetime number of uses. For example, some ECG lead sets are manufactured for a one-time use. The purpose of devices being manufactured for one-time use is because there may be reliability concerns if the single-use ECG lead set is used more than once. The ECG lead set 20 may keep track of its number of uses by incrementing a counter and storing the number of uses in the EEPROM 22. Alternatively, the patient monitor 7 may track the number of uses and write the number of uses into the EEPROM 22. Thus, the patient monitor 7 is capable of carrying out both read and write operations with respect to the EEPROM data.

The ECG extension cable 30 includes a first connector interface 31 at a first end that is configured to engage with the cable interface 11 of the patient monitor 7 and a second connector interface 32 at a second end that is configured to engage with the connector 21 of the patient monitor 7. Both connector interfaces 31 and 32 may be connectors arranged at the terminal ends of the extension cable 30 for the transmission of electrical signals between the ECG lead set 20 and the patient monitor 7.

The ECG extension cable 30 further includes circuitry 33 that enables both the prevention of ESU burns for patient safety and the transmission of EEPROM read or write data. While represented by a circuitry block, the circuitry components may be located anywhere along the ECG extension cable 30, including at connector interface 31, at connector interface 32, or along the cable itself. As will be described in further detail in FIG. 3, the circuitry 33 includes at least one series protection element 34 (e.g., a resistor and/or inductor, or multiples thereof) arranged in a ground path of the ECG extension cable 30. The series protection is an ESU protection element that is added to the ECG ground line and interferes with the EEPROM, thus preventing the EEPROM data from being read or written. However, the EEPROM Input/output line does not need ESU protection, as this line does not go to the patient.

The circuitry 33 further includes a switching element 35 (e.g., a switch or a multiplexer) connected in parallel to the series protection element 34 and configured to provide an electrical bypass path 36 that bypasses the series protection element 34. When the switch of the switching element 35 is closed, the bypass path 36 is completed and provides a low-resistive pathway or low-impedance pathway (e.g., a shorted pathway) relative to the electrical pathway through the series protection element 34. Thus, the series protection element 34 is bypassed and communication between the patient monitor 7 and the EEPROM 22 through the ECG extension cable 30 is enabled without being subjected to interference as would be the case if the series protection element 34 was not bypassed.

Figure 3:
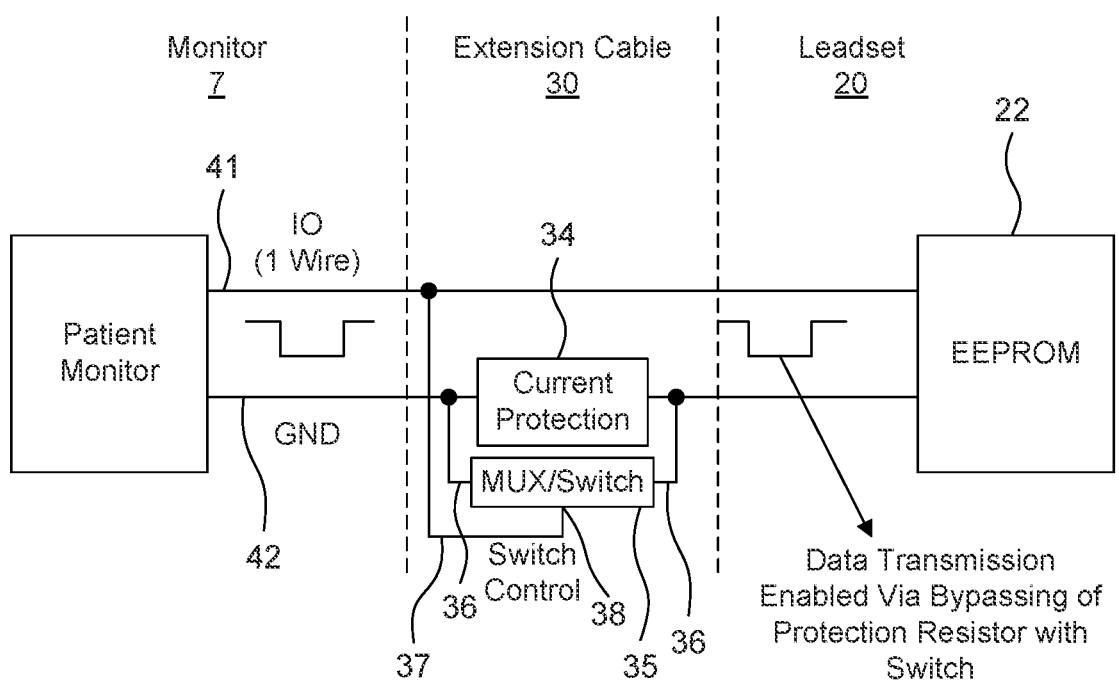
FIG. 3 shows a schematic block diagram of the ECG cable system and ECG monitoring device according to one or more embodiments.

FIG. 3 shows a schematic block diagram of the ECG cable system and ECG monitoring device according to one or more embodiments.

The ECG cable system includes a single EEPROM input/output (I/O) pathway 41 (i.e., a single I/O wire) that is configured to bidirectionally transmit EEPROM data between the EEPROM 22 and the patient monitor 7. Thus, the I/O pathway 41 extends from the patient monitor 7, through the ECG extension cable 30, to the EEPROM 22 at the ECG lead set 20. As such, the connector 21 includes an I/O pin or an I/O pin hole that interfaces with the I/O pathway 41 to compete the electrical pathway to the EEPROM 22.

In addition, the ECG cable system includes a ground (GND) pathway 42 (i.e., a ground wire) that provides a ground connection to the EEPROM 22 as well as to the lead set 20 in general. Thus, the ground pathway 42 extends from the patient monitor 7, through the ECG extension cable 30, to the EEPROM 22 at the ECG lead set 20. The series protection element 34 is connected in series along the ground pathway 42. The switching element 35 arranged along the bypass path 36 that is connected to the ground pathway 42 in parallel to the series protection element 34. As a result, one terminal end of the bypass path 36 is connected to an input of the series protection element 34 and a second terminal end of the bypass path 36 is connected to an output of the series protection element 34.

The circuitry 33 further includes a switch control signal path 37 coupled to the I/O pathway 41 and to a control input 38 of the switching element 35. The switching element 35 is configured to detect a timing, via the I/O pathway 41, that is safe to disengage the ESU protection provided by the series protection element 34 from the ground path by a bypassing the same through the bypass path 36.

In particular, an initial electrical I/O signal is transmitted along the I/O pathway 41 when the EEPROM 22 is first initially connected to the patient monitor 7 via the ECG extension cable 30. The switching element 35 is configured to automatically detect the initial I/O signal, or a portion thereof, at its control input 38 and automatically initiate the bypass of the series protection element 34 for a predetermined duration. In other words, the switch control signal is tapped from an initial electrical signal transmitted along the I/O pathway that is generated in response to the patient monitor 7 being coupled to the ECG lead set 20 via the ECG extension cable 30. The predetermined duration is long enough (e.g., up to a few milliseconds) to allow sufficient time for the exchange of EEPROM data (read and write operations and authentication data exchange for authentication verification). The predetermined duration starts at the time the initial electrical I/O signal is detected by the switching element 35 and ends when a counter of the switching element 35 reaches a timing threshold. In response to an expiration the predetermined duration, the switching element 35 is configured to disconnect the bypass path 36 by opening of a switch, thereby reengaging the series protection element 34 with the ground pathway 42.

Thus, in response to detecting the initial connection, the EEPROM data communication method includes bypassing the series protection element 34 coupled in series along a ground pathway 42 of the ECG extension cable 30 such that a ground signal is redirected through a switching element 35 of the ECG extension cable 30, thereby bypassing the series protection element 34 and preventing interference thereby. Subsequently, the method includes, in response to detecting the initial connection, starting a counter of the switching element 35, and disabling the bypass path in response to a counter value of the counter reaching a threshold value corresponding to a predetermined period, thereby restoring the ground path through the series protection element 34.

In this way, patient safety can be assured algorithmically. Electrosurgery is constantly monitored and the EEPROM 22 is read or written to only when deemed safe for the patient. The likelihood for ESU burn is at its lowest when the ECG lead set 20 is initially connected to the patient monitor 7 as it is unlikely that the electrosurgery will have started within a few milliseconds following the initial connection. Intrinsically, this method is safe as the ground path for electrosurgery current requires two lines to be shorted at the same time.

The patient monitor 7 may be further configured to detect whether it is connected directly to the ECG lead set 20 or indirectly connected to the ECG lead set 20 via the ECG extension cable 30 and change its filter settings accordingly. For example, in response to detecting the ECG extension cable 30, the patient monitor may automatically change its filter settings to ESU filter settings to prevent noise from corrupting its front end circuitry.

In particular, the ECG extension cable 30 of the aforedescribed embodiments may be used in ESU procedures to provide patient safety via the series protection element 34. Thus, the patient monitor 7 can detect whether an ESU procedure is taking place via detection of the ECG extension cable 30. An ESU signal is typically high frequency (e.g., >100 kHz) and high amplitude, while ECG signals are lower than 2 kHz. Therefore, filters are needed to filter out the ESU signals to allow reading of the ECG signals. By detecting the ECG extension cable 30, the patient monitor 7 can automatically adjust its filter settings to filter out the ESU signals.

While various embodiments have been disclosed, it will be apparent to those skilled in the art that various changes and modifications can be made which will achieve some of the advantages of the concepts disclosed herein without departing from the spirit and scope of the invention. It will be obvious to those reasonably skilled in the art that other components performing the same functions may be suitably substituted. It is to be understood that other embodiments may be utilized and structural or logical changes may be made without departing from the scope of the present invention. It should be mentioned that features explained with reference to a specific figure may be combined with features of other figures, even in those not explicitly mentioned. Such modifications to the general inventive concept are intended to be covered by the appended claims and their legal equivalents.

Furthermore, the following claims are hereby incorporated into the detailed description, where each claim may stand on its own as a separate example embodiment. While each claim may stand on its own as a separate example embodiment, it is to be noted that—although a dependent claim may refer in the claims to a specific combination with one or more other claims—other example embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having means for performing each of the respective acts of these methods. For example, the techniques described in this disclosure may be implemented, at least in part, in hardware, software, firmware, or any combination thereof. For example, various aspects of the described techniques may be implemented within one or more processors, including one or more microprocessors, DSPs, ASICs, or any other equivalent integrated or discrete logic circuitry, as well as any combinations of such components.

Further, it is to be understood that the disclosure of multiple acts or functions disclosed in the specification or in the claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

What is claimed is:

1. An electrocardiogram (ECG) extension cable, comprising:
    a first connector configured to be electrically coupled to a physiological monitoring device;
    a second connector configured to be electrically coupled to an ECG lead set comprising a processor and a plurality of ECG leads;
    an input/output (I/O) wire configured to transmit ECG lead set data between the physiological monitoring device and the processor, wherein the ECG lead set data comprises at least one selected from the group of a number of leads in the plurality of ECG leads, ECG lead set authentication information, and a number of uses of the ECG lead set;
    a ground wire that establishes a ground path between the first connector and the second connector;
    a series protection element coupled in series along the ground wire; and
    a switching element coupled to the ground wire in parallel to the series protection element, thereby providing a bypass path, the bypass path providing a second ground path between the first connector and the second connector, the switching element being adapted to detect an initial electrical I/O signal transmitted on the I/O wire;
    wherein the switching element is adapted to close the bypass path when the initial electrical I/O signal is detected, maintain the bypass path in a closed position for a predetermined period of time, and open the bypass path at the end of the predetermined period of time.

2. The ECG extension cable of claim 1, wherein:
    the switching element includes an input configured to receive a switch control signal, and
    in response to receiving the switch control signal, the switching element is configured to enable the bypass path, thereby bypassing the series protection element.

3. The ECG extension cable of claim 2, wherein:
    the switching element is configured to enable the bypass path for a predetermined period initiated by the switch control signal, and
    the switching element is configured to disable the bypass path in response to an expiration of the predetermined period, thereby restoring the ground path along the series protection element.

4. The ECG extension cable of claim 2, wherein the bypass path has a lower impedance when enabled than the series protection element.

5. The ECG extension cable of claim 2, wherein the bypass path is a shorted pathway when enabled by the switching element.

6. The ECG extension cable of claim 2, wherein:
    the input of the switching element is electrically connected to the I/O wire, and
    the switch control signal is received from the I/O wire.

7. The ECG extension cable of claim 6, wherein the switch control signal is tapped from an initial electrical signal transmitted along the I/O wire that is generated in response to the physiological monitoring device being coupled to the ECG lead set.

8. The ECG extension cable of claim 7, wherein:
    the switching element is configured to enable the bypass path for a predetermined period initiated by the switch control signal, and
    the switching element is configured to disable the bypass path in response to an expiration of the predetermined period, thereby restoring the ground path along the series protection element.

9. The ECG extension cable of claim 6, wherein the switching element is a multiplexer comprising a switch that, when closed, completes the bypass path.

10. The ECG extension cable of claim 1, wherein the series protection element includes at least one resistor or at least one inductor.

11. The ECG extension cable of claim 1, wherein the initial electrical I/O signal comprises the ECG lead set data.

12. The ECG extension cable of claim 1, wherein the processor comprises an electrically erasable programmable read-only memory (EEPROM), the input/output (I/O) wire is an EEPROM I/O wire, and the data is EEPROM data.

13. An electrocardiogram (ECG) system, comprising:
an ECG lead set comprising a plurality of leads configured to measure ECG electrical signals and a processor configured to store ECG lead set data;
a physiological monitoring device configured to receive and monitor the ECG electrical signals; and
an ECG extension cable coupled to and between the ECG lead set and the physiological monitoring device, wherein the ECG extension cable comprises:
 a first connector configured to be electrically coupled to the physiological monitoring device;
 a second connector configured to be electrically coupled to the ECG lead set comprising a plurality of ECG leads;
 an input/output (I/O) wire configured to transmit the ECG lead set data between the physiological monitoring device and the processor, wherein the ECG lead set data comprises at least one selected from the group of a number of leads in the plurality of ECG leads, ECG lead set authentication information, and a number of uses of the ECG lead set;
 a ground wire that establishes a ground path between the first connector and the second connector;
 a series protection element coupled in series along the ground wire; and
 a switching element coupled to the ground wire in parallel to the series protection element, thereby providing a bypass path, the bypass path providing a second ground path between the first connector and the second connector, the switching element being adapted to detect an initial electrical I/O signal transmitted on the I/O wire;
 wherein the switching element is adapted to close the bypass path when the initial electrical I/O signal is detected, maintain the bypass path in a closed position for a predetermined period of time, and open the bypass path at the end of the predetermined period of time.

14. The ECG system of claim 13, wherein:
the switching element includes an input configured to receive a switch control signal, and
in response to receiving the switch control signal, the switching element is configured to enable the bypass path, thereby bypassing the series protection element.

15. The ECG system of claim 14, wherein:
the switching element is configured to enable the bypass path for a predetermined period initiated by the switch control signal, and
the switching element is configured to disable the bypass path in response to an expiration of the predetermined period, thereby restoring the ground path along the series protection element.

16. The ECG system of claim 14, wherein the bypass path has a lower impedance when enabled than the series protection element.

17. The ECG system of claim 14, wherein the bypass path is a shorted pathway when enabled by the switching element.

18. The ECG system of claim 14, wherein:
the input of the switching element is electrically connected to the I/O wire, and
the switch control signal is received from the I/O wire.

19. The ECG system of claim 18, wherein the switch control signal is tapped from an initial electrical signal transmitted along the I/O wire that is generated in response to the physiological monitoring device being coupled to the ECG lead set.

20. The ECG system of claim 19, wherein:
the switching element is configured to enable the bypass path for a predetermined period initiated by the switch control signal, and
the switching element is configured to disable the bypass path in response to an expiration of the predetermined period, thereby restoring the ground path along the series protection element.

21. The ECG system of claim 18, wherein the switching element is a multiplexer comprising a switch that, when closed, completes the bypass path.

22. The ECG system of claim 13, wherein the series protection element is an electrosurgical protection element.

23. The ECG system of claim 13, wherein the initial electrical I/O signal comprises the ECG lead set data.

24. The ECG system of claim 13, wherein the processor comprises an electrically erasable programmable read-only memory (EEPROM), the input/output (I/O) wire is an EEPROM I/O wire, and the data is EEPROM data.

25. The ECG system of claim 13, wherein:
the ECG extension cable is an electrosurgical unit extension cable and the series protection element is an electrosurgical unit series protection element, and
the physiological monitoring device comprises at least one adjustable filter setting, and the physiological monitoring device is configured to automatically detect the electrosurgical unit extension cable and automatically adjust the at least one adjustable filter setting to filter electrosurgical unit signals from ECG signals in response to detecting the electrosurgical unit extension cable.

* * * * *